(12) United States Patent
Park et al.

(10) Patent No.: US 10,792,806 B2
(45) Date of Patent: Oct. 6, 2020

(54) DEVICE FOR DRIVING ARTIFICIAL MUSCLE MODULE AND METHOD FOR DRIVING ARTIFICIAL MUSCLE MODULE

(71) Applicant: KOREA INSTITUTE OF MACHINERY & MATERIALS, Daejeon (KR)

(72) Inventors: Cheol-hoon Park, Daejeon (KR); Young-su Son, Daejeon (KR); Sang-yong Ham, Daejeon (KR); Sang-kyu Choi, Daejeon (KR); Doo-euy Hong, Daejeon (KR); Kyung-jun Choi, Daejeon (KR); Seong-joon Park, Daejeon (KR)

(73) Assignee: KOREA INSTITUTE OF MACHINERY & MATERIALS, Daejeon (KR)

( * ) Notice: Subject to any disclaimer, the term of this patent is extended or adjusted under 35 U.S.C. 154(b) by 154 days.

(21) Appl. No.: 16/091,370

(22) PCT Filed: Nov. 30, 2017

(86) PCT No.: PCT/KR2017/013907
§ 371 (c)(1),
(2) Date: Oct. 4, 2018

(87) PCT Pub. No.: WO2018/110874
PCT Pub. Date: Jun. 21, 2018

(65) Prior Publication Data
US 2019/0152052 A1    May 23, 2019

(30) Foreign Application Priority Data
Dec. 14, 2016 (KR) .......................... 10-2016-0170534

(51) Int. Cl.
*B25J 9/10* (2006.01)
*A61F 2/68* (2006.01)
(Continued)

(52) U.S. Cl.
CPC ............... *B25J 9/1085* (2013.01); *A61F 2/68* (2013.01); *B25J 9/1075* (2013.01); *A61F 2002/5066* (2013.01); *A61F 2002/745* (2013.01)

(58) Field of Classification Search
CPC .............................. B25J 9/1085; B25J 9/1075
See application file for complete search history.

(56) References Cited

U.S. PATENT DOCUMENTS 5,645,520 A * 7/1997 Nakamura ........... A61B 1/0058
600/143
6,168,634 B1 1/2001 Schmitz
(Continued)

FOREIGN PATENT DOCUMENTS

JP     2011-148037 A    8/2011
KR     100911269 B1     8/2009
(Continued)

OTHER PUBLICATIONS

International Search Report dated Mar. 9, 2018, corresponding to International Application No. PCT/KR2017/013907 citing the above reference(s).
(Continued)

*Primary Examiner* — Shafiq Mian
(74) *Attorney, Agent, or Firm* — Hauptman Ham, LLP

(57) ABSTRACT

In a driving device of an artificial muscle module and a driving method thereof, the driving device includes a fluid tank unit, a fluid providing line, a fluid collecting line, a circulation pump unit, a temp control unit and a fluid distributing unit. The fluid providing line includes high temp
(Continued)

and low temp water tanks. The fluid providing line connects a first side of the artificial muscle module to the fluid tank unit. The fluid collecting line connects a second side of the artificial muscle module to the fluid tank unit. The circulation pump unit is positioned at least one of the fluid providing line and the fluid collecting line. The temp control unit controls temperature of the fluid. The fluid distributing unit is positioned at the fluid collecting line, and distributes the fluid in the fluid collecting line.

9 Claims, 9 Drawing Sheets

(51) Int. Cl.
*A61F 2/50* (2006.01)
*A61F 2/74* (2006.01)

(56) References Cited

U.S. PATENT DOCUMENTS

| | | |
|---|---|---|
| 2010/0268352 A1 | 10/2010 | Majoe |
| 2016/0206420 A1 | 7/2016 | Yun et al. |

FOREIGN PATENT DOCUMENTS

| | | |
|---|---|---|
| KR | 1020160013663 A | 2/2016 |
| KR | 1020160043242 A | 4/2016 |
| KR | 1020160088093 A | 7/2016 |
| KR | 101650465 B1 | 8/2016 |
| KR | 1020160117658 A | 10/2016 |

OTHER PUBLICATIONS

The extended European Search Report dated Apr. 8, 2020 in connection with the counterpart European Patent Application No. 17882144.3, citing the above reference(s).

\* cited by examiner

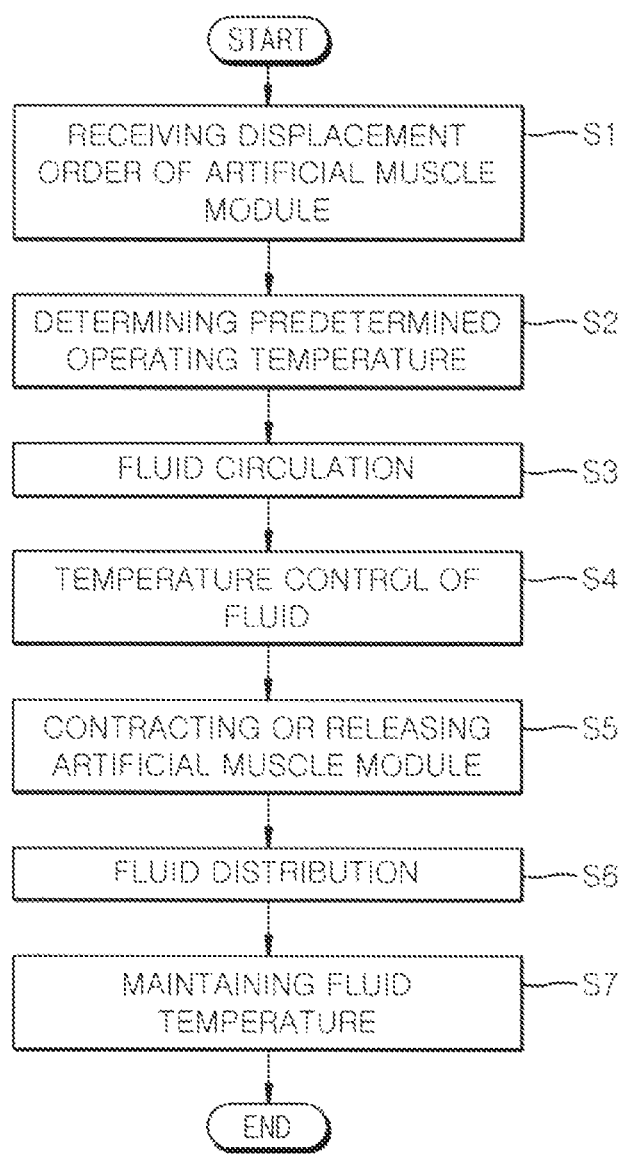

DEVICE FOR DRIVING ARTIFICIAL MUSCLE MODULE AND METHOD FOR DRIVING ARTIFICIAL MUSCLE MODULE

CROSS REFERENCE TO RELATED APPLICATION

This present application is a national stage filing under 35 U.S.C § 371 of PCT application number PCT/KR2017/013907 filed on Nov. 30, 2017 which is based upon and claims the benefit of priority to Korean Patent Application No. 10-2016-0170534 filed on Dec. 14, 2016 respectively in the Korean Intellectual Property Office. The disclosures of the above-listed applications are hereby incorporated by reference herein in their entirety.

BACKGROUND

1. Field of Disclosure

The present disclosure of invention relates a driving device of an artificial muscle module and a driving method of the artificial muscle module, and more specifically the present disclosure of invention relates to a driving device of an artificial muscle module and a driving method of the artificial muscle module, performing a flexible movement of the artificial muscle module and increasing a response of the artificial muscle module according to a temperature of a fluid charged in the artificial muscle module, and increasing energy efficiency.

2. Description of Related Technology

Generally, a living body muscle is reacted by an electric signal transmitted from neuron (a nerve cell). Likewise, an artificial muscle is manufactured to be reacted by an external electric input and may replace the living body muscle.

The artificial muscle may be used for a rehabilitation robot functioning an arm or a leg of a disabled person, a working robot working in special circumstances such as the space, the ocean and a nuclear power plant, and a high technology device such as MEMS performing a high complex motion with a small size.

A heat response driving device contracting or expanding according to a temperature, such as a shape-memory alloy (SMA), a shape-memory resin, a carbon nanotube, a nylon and so on, is used in the artificial muscle.

For example, the shape-memory alloy needs an effective heating/cooling system for performing a high response motion speed. Thus, conventionally, a heating method using electric resistance is used, and a cooling method using an air or a water is used.

However, in the heating method using the electric resistance, response speed of the artificial muscle is relatively bad, energy consumption is increased, power source is increased to increase load capacity of the artificial muscle, and insulation is necessary.

Thus, a method for driving the artificial muscle may be necessary to enhance the conventional driving method.

Related prior art is Korean patent No. 10-0911269 which is disclosed on Aug. 11, 2009 and is a driving supporting apparatus and a driving supporting method.

SUMMARY

The present invention is developed to solve the above-mentioned problems of the related arts. The present invention provides a driving device of an artificial muscle module and a driving method of artificial muscle module, capable of performing a flexible movement of the artificial muscle module and increasing a response of the artificial muscle module according to a temperature of a fluid charged in the artificial muscle module, and increasing energy efficiency.

According to an example embodiment, the artificial muscle module contains a fluid and a heat reaction driving unit. The heat reaction driving unit is deformed in a shape in response to temperature of the fluid. The driving device includes a fluid tank unit, a fluid providing line, a fluid collecting line, a circulation pump unit, a temp control unit and a fluid distributing unit. The fluid tank unit includes a high temp water tank containing a relatively high temperature fluid, and a low temp water tank containing a relatively low temperature fluid. The fluid providing line connects a first side of the artificial muscle module to the fluid tank unit, to provide the fluid to the artificial muscle module. The fluid collecting line connects a second side of the artificial muscle module to the fluid tank unit, to collect the fluid charged in the artificial muscle module. The circulation pump unit is positioned at least one of the fluid providing line and the fluid collecting line, to circulate the fluid between the artificial muscle module and the fluid tank unit. The temp control unit controls temperature of the fluid to be provided to the artificial muscle module using the fluid discharged from the high temp water tank and the low temp water tank. The temp control unit is positioned at the fluid providing line. The fluid distributing unit is positioned at the fluid collecting line, and distributes the fluid in the fluid collecting line to the high temp water tank or the low temp water tank.

In an example, the fluid tank unit may further include a heating unit for heating the fluid in the high temp water tank, to maintain the fluid in the high temp water tank to be in a predetermined high temperature.

In an example, the fluid tank unit may further include a cooling unit for cooling the fluid in the low temp water tank, to maintain the fluid in the low temp water to be in a predetermined low temperature.

In an example, the temp control unit may include a first control valve for controlling an amount of the fluid discharged from the high temp water tank, and a second control valve for controlling an amount of the fluid discharged from the low temp water tank. The amount of the fluid discharged from the high temp water tank and that from the low temp water tank may be decided such that the fluid passing through the temp control unit has a predetermined operating temperature.

In an example, the temp control unit may include a discharge control valve for discharging the fluid by controlling the fluid discharged from the low temp water tank considering the amount of the fluid discharged from the high temp water tank. A ratio between the amount of the fluid discharged from the high temp water tank and that from the low temp water tank may be controlled by the discharge control valve, such that the fluid passing through the temp control unit has a predetermined operating temperature.

In an example, the fluid distributing unit may include a first distributing valve for distributing the fluid collected from the fluid circulation line to the high temp water tank, and a second distributing valve for distributing the fluid collected from the fluid circulation line to the low temp water tank. The first distributing valve or the second distributing valve may be operated based on a predetermined distributing condition, so as to distribute the fluid collected from the fluid collecting line to the high temp water tank or the low temp water tank.

In an example, the fluid distributing unit may include a collected fluid for distributing valve distributing the fluid collected from the fluid collecting line to the high temp water tank or the low temp water tank. The collected fluid distributing valve may be operated based on a predetermined distributing condition, so as to distribute the fluid collected from the fluid collecting line to the high temp water tank or the low temp water tank.

In an example, the driving device may further include a control unit for determining an operating temperature of a fluid for deforming a shape of the artificial muscle module based on a displacement command, to control the circulation pump unit, the temp control unit and the fluid distributing unit.

According to another example embodiment, in the driving method, a displacement command is received for deforming a shape of the artificial muscle module. An operating temperature of a fluid is determined for deforming the shape of the artificial muscle module based on the displacement command. The fluid is circulated between the artificial muscle module and the fluid tank unit. A fluid is controlled to be at the operating temperature using a fluid discharged from a high temp water tank and a low temp water tank. The fluid at the operating temperature is provided to the artificial muscle module. The fluid is collected from the artificial muscle module and the fluid is distributed to the high temp water tank or the low temp water tank, based on a distributing condition.

In an example, the temperature of the fluid in the high temp water tank is maintained to be a predetermined high temperature, or the temperature of the fluid in the low temp water tank is maintained to be a predetermined low temperature, corresponding to the fluid flowed into or discharged from the fluid tank unit.

According to the present example embodiments, a flexible movement of the artificial muscle module may be performed and a response of the artificial muscle module may be increased according to a temperature of a fluid charged in the artificial muscle module, and energy efficiency may be increased.

In addition, a predetermined high temperature fluid and a predetermined low temperature fluid are decided variously, and thus the operating temperature necessary for contracting or relaxing the heat reaction driving unit, and a displacement of the artificial muscle module may be easily controlled.

In addition, the predetermined high temperature and the predetermined low temperature may be easily maintained, and the temperature of the fluid in the fluid tank unit is less changed, to meet the operating temperature in mixing the fluid, very conveniently.

In addition, the operating temperature may be easily performed, and an amount of the fluid provided to the artificial muscle module may be easily controlled.

In addition, the ratio of the fluid for performing the operating temperature may be easily controlled, and the fluid discharged from the fluid tank unit may be easily stabilized.

In addition, the fluid discharged from the artificial muscle module may be easily collected, and the temperature of the fluid in the fluid tank unit may be less changed. Thus, the temperature of the fluid in the fluid tank unit may be easily maintained.

In addition, the fluid discharged from the artificial muscle module may be distributed more clearly, and thus the fluid tank unit may be prevented from being malfunctioned in maintaining the temperature of the fluid according to the fluid collected from the fluid tank unit.

In addition, the temperature of the fluid provided to the artificial muscle module is variously changed to perform the flexibility of the artificial muscle module very similar to a living body muscle.

BRIEF DESCRIPTION OF THE DRAWINGS

FIG. 9 is a driving method of the artificial muscle module using the driving device of the artificial muscle module of FIG. 1.

* Reference Numeral

Figure 1:
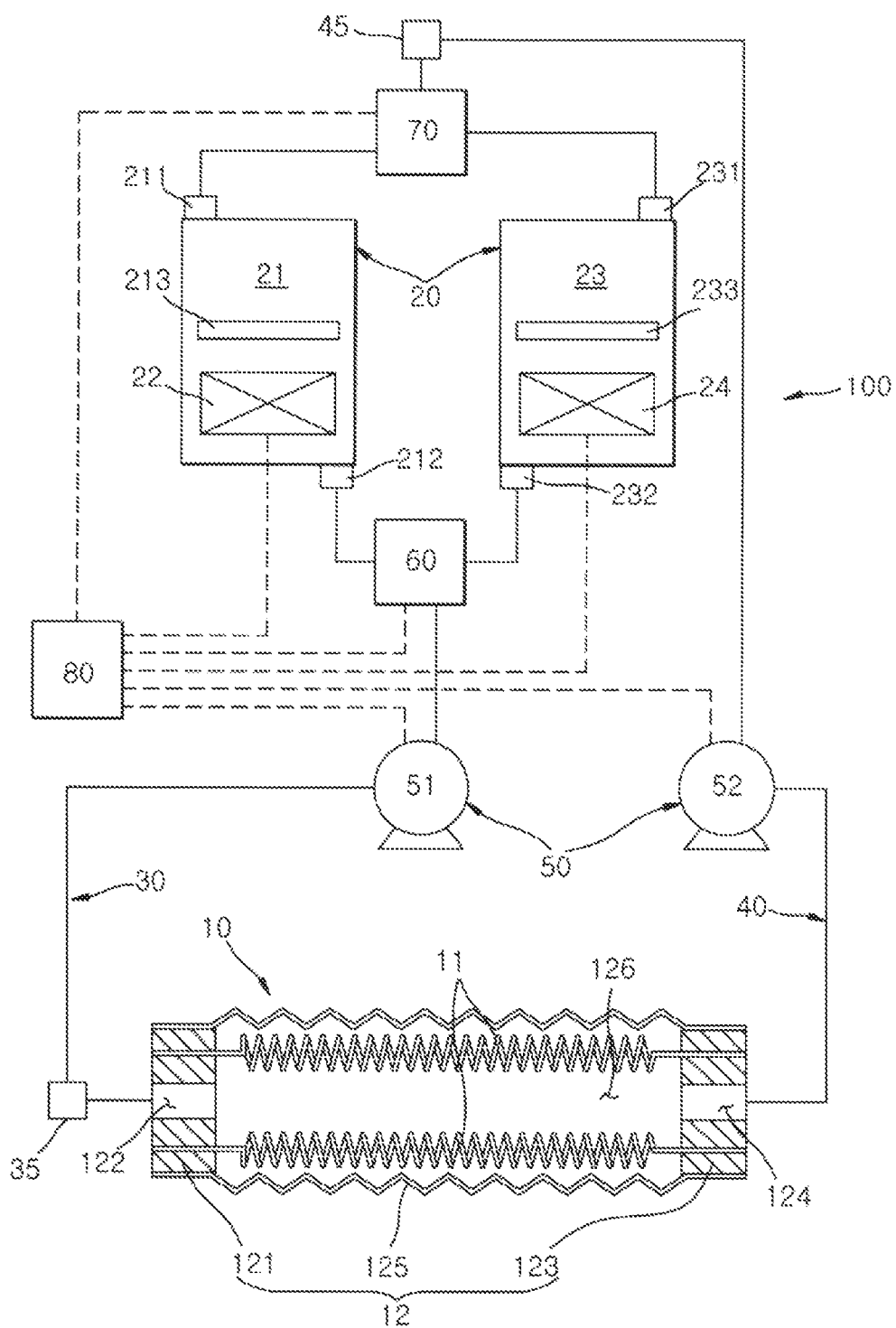
FIG. 1 is a schematic diagram illustrating a driving device of an artificial muscle module according to an example embodiment of the present invention.

10: artificial muscle module 11: shape-memory allow spring 12: casing unit

121: first closure 122: fluid inlet 123: second closure

124: fluid outlet 125: stretching conduit 126: inner space

20: fluid tank unit 21: high temp water tank 211: high temp water inlet

212: high temp water outlet 213: high temp water distributer 22: heating unit

23: low temp water tank 231: low temp water inlet 232: low temp water outlet

233: low temp water distributer 24: cooling unit 30: fluid providing line

31: first providing line 32: second providing line 33: merging providing line

35: providing temp sensor 40: fluid collecting line 41: first collecting line

42: second collecting line 43: distributing collecting line 45: collecting temp sensor 50: circulation pump unit 51: first pump 52: second pump 60: temp control unit 61: first control valve 62: second control valve 63: discharge control valve 631: discharge control path 632: first inlet 633: second inlet 634: outlet diverging path 635: operating fluid provider 636: discharge control block 637: control driver 64: providing fluid mixer 70: fluid distributing unit 71: first distributing valve 72: second distributing valve 73: collected fluid distributing valve 731: collecting distributing path 732: first outlet 733: second outlet 734: inlet diverging path 735: collecting fluid inlet

736: collecting distributing block 737: distributing driver 80: control unit

81: displacement receiver 82: temp determiner 83: control unit controller

84: distributing unit controller 85: pump controller 86: high temp water controller

87: low temp water controller S1: displacement receiving step S2: tem determining step

S3: fluid circulating step S4: temp control step S5: module operating step

S6: fluid distributing step S7: fluid temp maintaining step

DETAILED DESCRIPTION

The invention is described more fully hereinafter with reference to the accompanying drawings, in which embodiments of the invention are shown. This invention may, however, be embodied in many different forms and should not be construed as limited to the embodiments set forth herein. Rather, these embodiments are provided so that this disclosure will be thorough and complete, and will fully convey the scope of the invention to those skilled in the art. Same elements or components are expressed with same reference numerals in the drawings.

Figure 2:
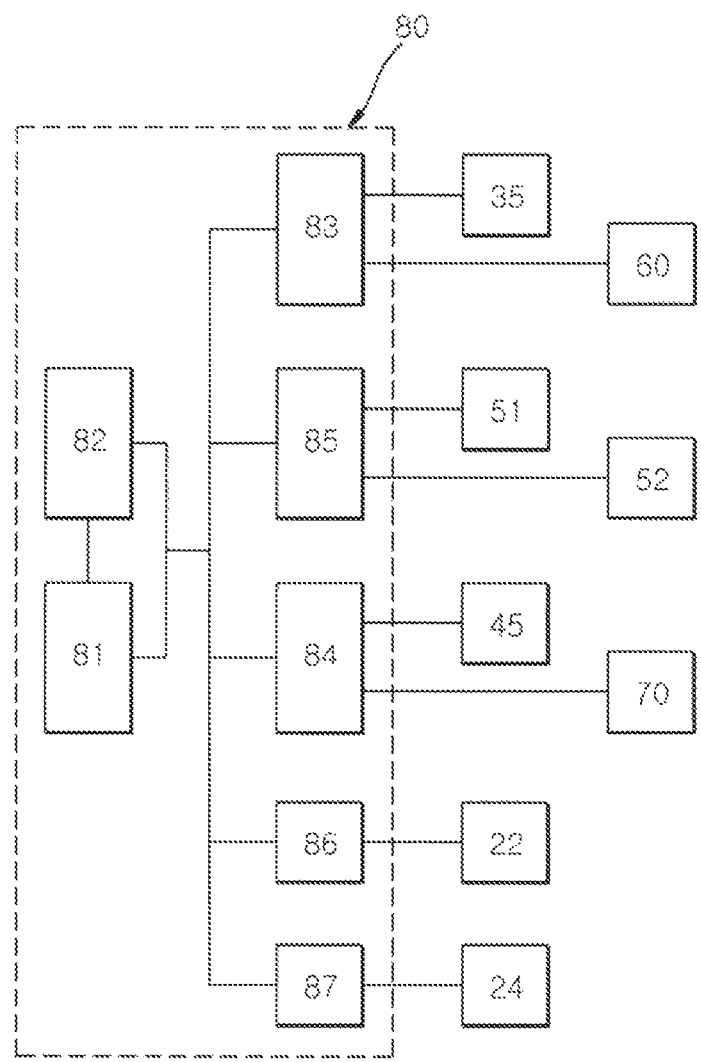
FIG. 2 is a schematic diagram illustrating a control unit of the driving device of the artificial muscle module of FIG. 1.
Figure 3:
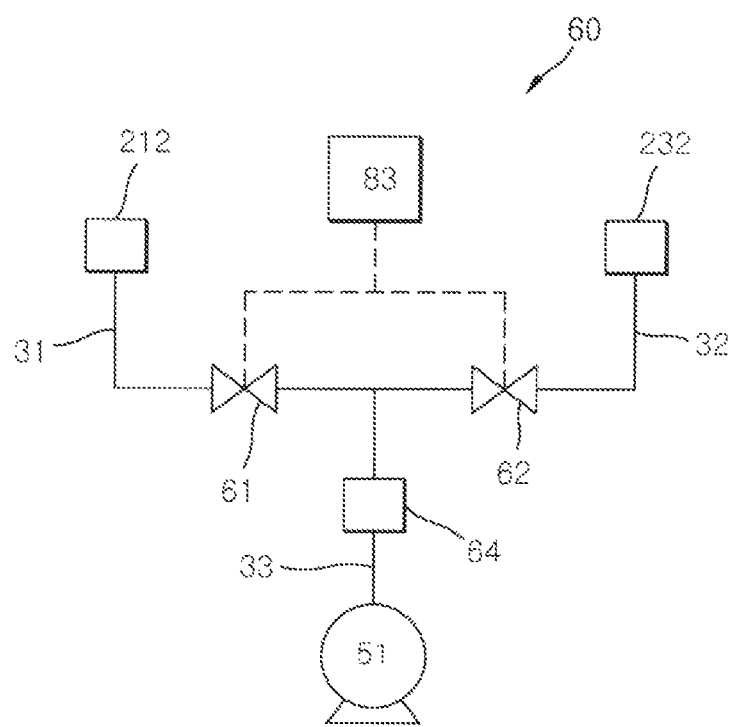
FIG. 3 is a schematic diagram illustrating an example temperature control unit of the driving device of the artificial muscle module of FIG. 1.
Figure 4:
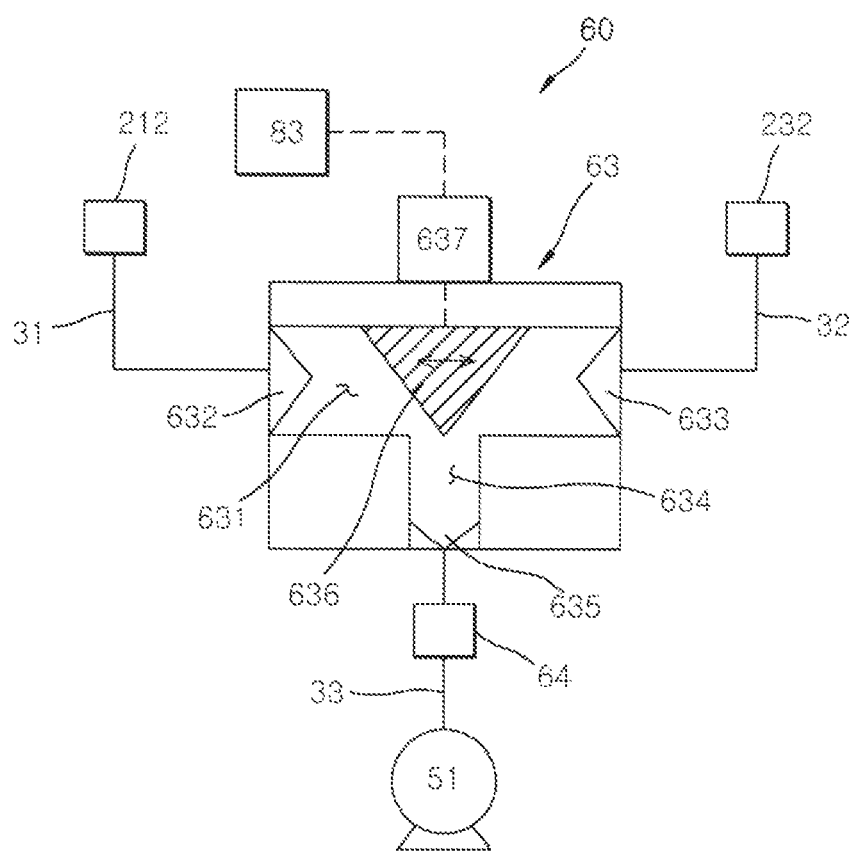
FIG. 4 is a schematic diagram illustrating another example temperature control unit of the driving device of the artificial muscle module of FIG. 1.
Figure 5:
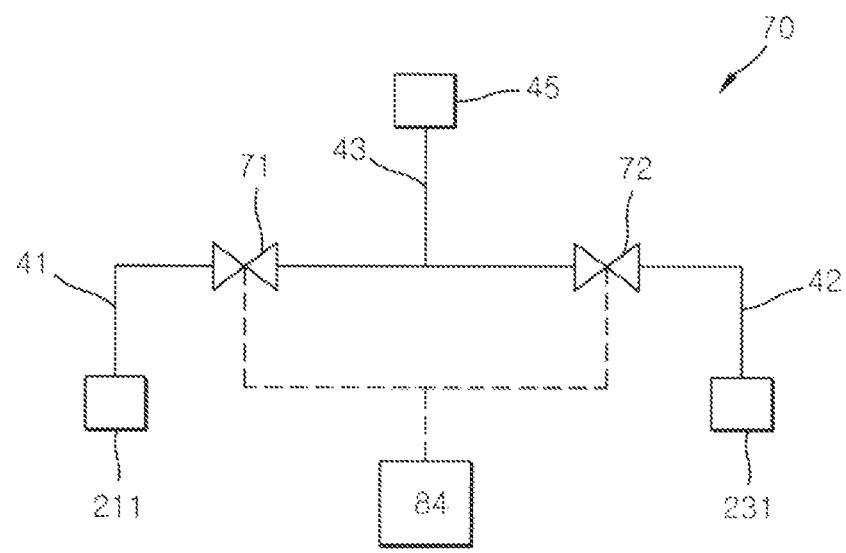
FIG. 5 is a schematic diagram illustrating an example fluid distributing unit of the driving device of the artificial muscle module of FIG. 1.
Figure 6:
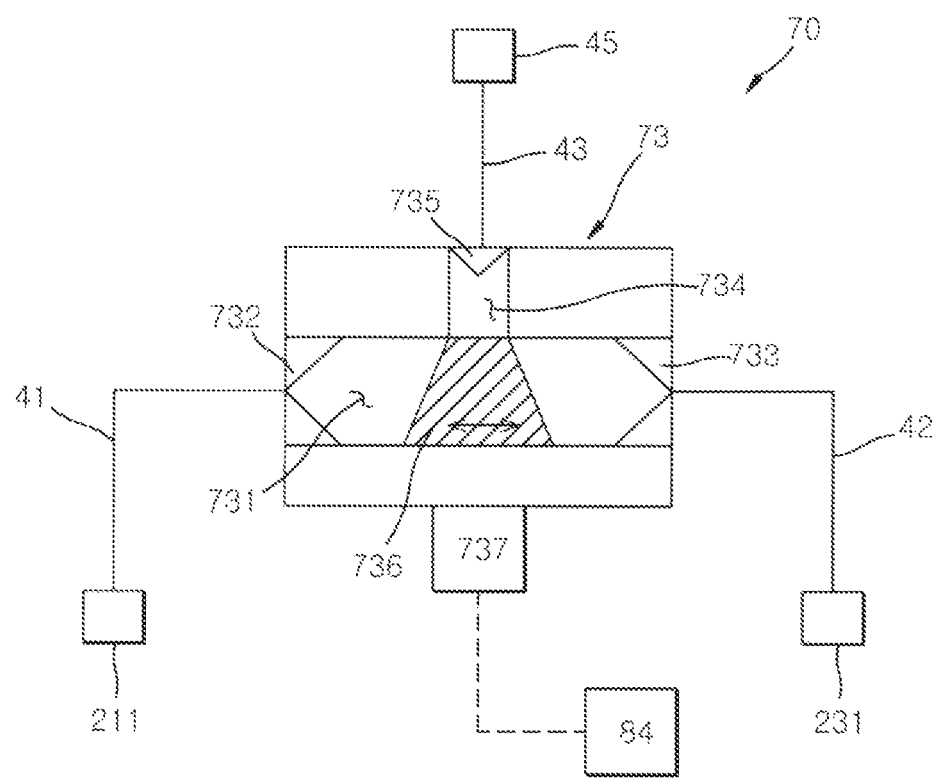
FIG. 6 is a schematic diagram illustrating another example fluid distributing unit of the driving device of the artificial muscle module of FIG. 1.
Figure 7:
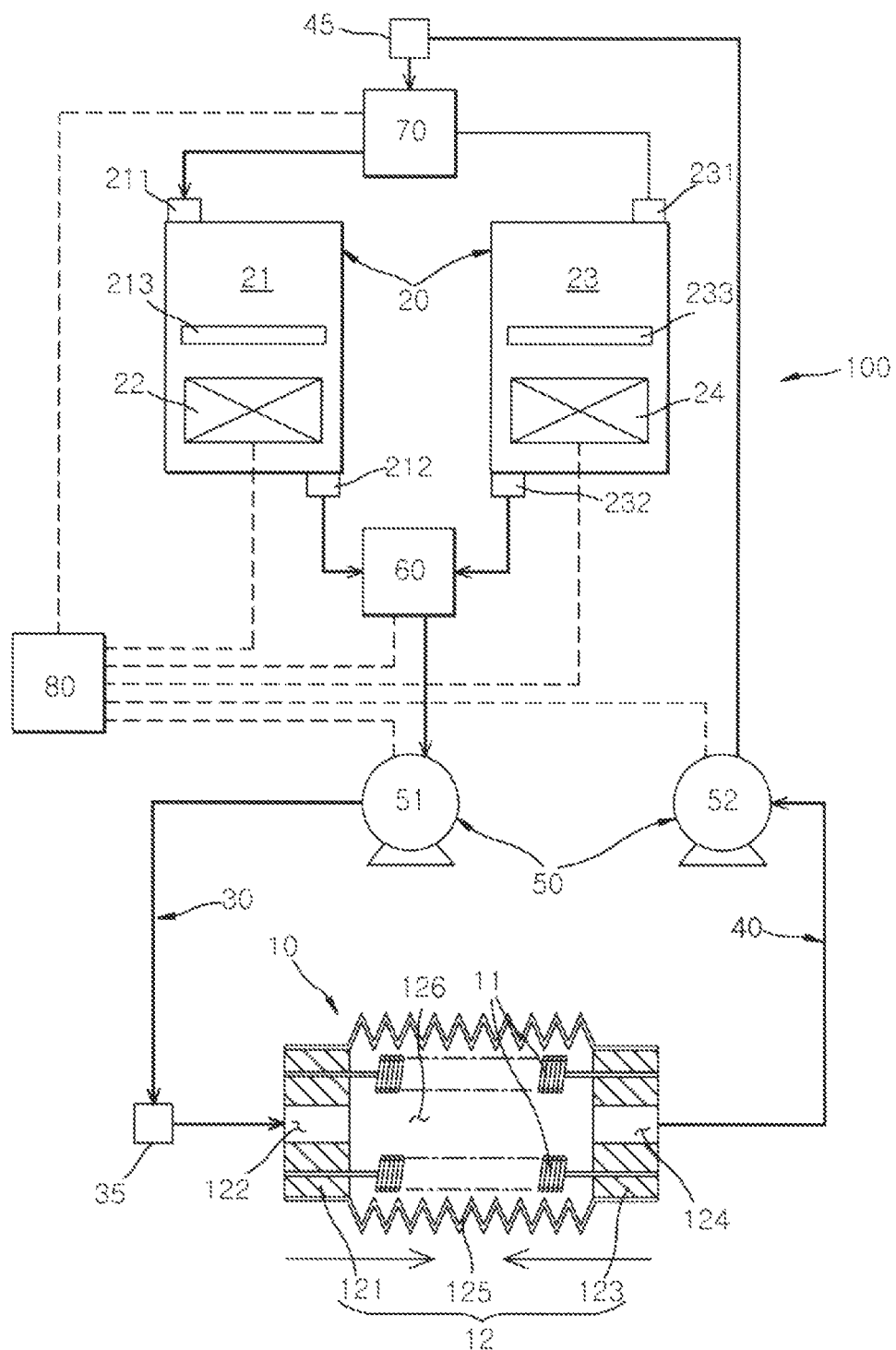
FIG. 7 is a schematic diagram illustrating a contracting state of the driving device of the artificial muscle module of FIG. 1.
Figure 8:
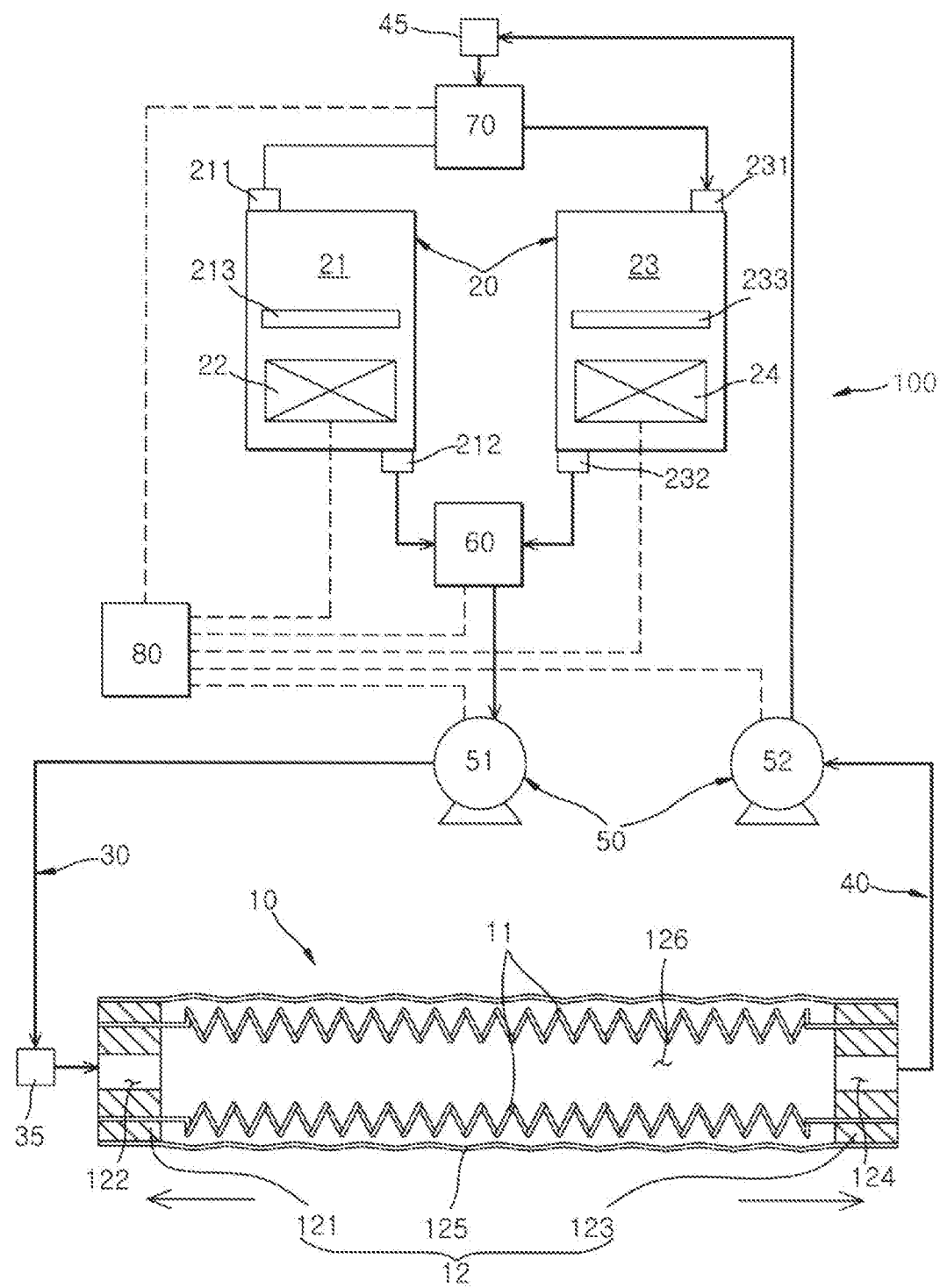
FIG. 8 is a schematic diagram illustrating a relaxed state of the driving device of the artificial muscle module of FIG. 1.

FIG. 1 is a schematic diagram illustrating a driving device of an artificial muscle module according to an example embodiment of the present invention. FIG. 2 is a schematic diagram illustrating a control unit of the driving device of the artificial muscle module of FIG. 1. FIG. 3 is a schematic diagram illustrating an example temperature control unit of the driving device of the artificial muscle module of FIG. 1. FIG. 4 is a schematic diagram illustrating another example temperature control unit of the driving device of the artificial muscle module of FIG. 1. FIG. 5 is a schematic diagram illustrating an example fluid distributing unit of the driving device of the artificial muscle module of FIG. 1. FIG. 6 is a schematic diagram illustrating another example fluid distributing unit of the driving device of the artificial muscle module of FIG. 1. FIG. 7 is a schematic diagram illustrating a contracting state of the driving device of the artificial muscle module of FIG. 1. FIG. 8 is a schematic diagram illustrating a relaxed state of the driving device of the artificial muscle module of FIG. 1.

Referring to FIGS. 1 to 8, the driving device 100 of the artificial muscle module 10 according to the present example embodiment, contracts or relaxes the artificial muscle module 10.

First, the artificial muscle module 10 includes a heat reaction driving unit, and a casing unit 12. The heat reaction driving unit is reacted to a heat and a shape of the heat reaction driving unit is deformed. The casing unit 12 forms an inner space 126 in which a fluid is charged, and is connected to the heat reaction driving unit. The casing unit 12 is deformed with the heat reaction driving unit.

The heat reaction driving unit may include a shape-memory alloy spring 11 reacted to the heat. The shape-memory alloy spring 11 may be manufactured using a shape-memory alloy material wire, and may be contracted or relaxed by the heat.

In the present example embodiment, the heat reaction driving unit includes a pair of the shape-memory alloy springs, and the pair of the shape-memory alloy springs are arranged in parallel, but not limited thereto. The number of the shape-memory alloy springs may be at least one, and may be changed variously, considering load capacity of the artificial muscle module 10.

The heat reaction driving unit may include various kinds of heat reacted materials, such as a shape memory resin, a shape memory polymer, a carbon nanotube, polyethylene, polyamide, nylon and so on.

The casing unit 12 includes a stretching conduit 125 being stretchable, a first closure 121 disposed at a first end of the stretching conduit 125, and a second closure 123 disposed at a second end of the stretching conduit 125.

The stretching conduit 125 may be a corrugate tube or a bellows tube, but not limited thereto. The stretching conduit 125 may be any material or structure capable of being deformed due to an external force.

Thus, the first closure 121 is enclosed with the first end of the stretching conduit 125, and the second closure 123 is enclosed with the second end of the stretching conduit 125, to form the inner space 126 inside of the casing unit 12.

A fluid inlet 122 is formed through the first closure 121, and a fluid operating the artificial muscle module 10 is flowed into the inner space 126 through the fluid inlet 122. A fluid outlet 124 is formed through the second closure 123, and a fluid is discharged from the inner space 126 through the fluid outlet 124.

In addition, a first combining portion is formed at the first closure 121, and a first end of the shape-memory alloy spring 11 is combined with the first combining portion. A second combining portion is formed at the second closure 123, and a second end of the shape-memory alloy spring 11 is combined with the second combining portion.

When the shape-memory alloy spring 11 is contracted or relaxed, the first and second closures 121 and 123 moves together along a longitudinal direction of the shape-memory alloy spring 11, and thus the stretching conduit 125 combined with the first and second closures 121 and 123 is contracted or relaxed.

Here, the first and second closures 121 and 123 may have heat resistance to temperature change of the shape-memory alloy spring 11.

Further, a first sealing member may be formed at the first combining portion combined with the first end of the shape-memory alloy spring 11, and a second sealing member may be formed at the second combining portion combined with the second end of the shape-memory alloy spring 11.

The driving device 100 of the artificial muscle module includes a fluid tank unit 20, a fluid providing line 20, a fluid collecting line 40, a circulation pump unit 50, a temp control unit 60 and a fluid distributing unit 70. Hereinafter, 'temp' is abbreviation of 'temperature'.

A heated fluid and a cooled fluid are contained in the fluid tank unit 20. The fluid tank unit 20 includes a high temp water tank 21 containing a fluid having a predetermined relatively high temperature, and a low temp water tank 23 containing a fluid having a predetermined relatively low temperature. Here, the relatively high temperature is higher than the relatively low temperature, and may be predetermined by an operator. Likewise the relatively low temperature may also be predetermined by the operator. Thus, the relatively high temperature may be a first temperature, and the relatively low temperature may be a second temperature lower than the first temperature.

Here, the fluid tank unit 20 may further include a heating unit 22. The heating unit 22 heats the fluid in the high temp water tank 21, to maintain the temperature of the fluid in the high temp water tank 21 to be a predetermined high temperature. However, various kinds of heating device may be applied stead of the heating unit 22, to have a function mentioned above.

In addition, the fluid tank unit 20 may further include a cooling unit 24. The cooling unit 24 cools the fluid in the low temp water tank 23, to maintain the temperature of the fluid in the low temp water tank 23 to be a predetermined low temperature. However, various kinds of cooling device may be applied stead of the cooling unit 24, to have a function mentioned above.

The high temp water tank 21 includes a high temp water inlet 211, a high temp water outlet 212, and a high temp water distributer 213. The fluid is flowed through the high temp water inlet 211. The fluid is discharged through the high temp water outlet 212. The high temp water distributer 213 divides an inside of the high temp water tank 21 into a high temp mixing portion and a high temp maintaining portion. The fluid flowed from the high temp water inlet 211 and the fluid in the high temp water tank 21 are mixed in the high temp mixing portion. The mixed fluid in the high temp mixing portion is maintained to be a predetermined high temperature in the high temp maintaining portion. In the high temp maintaining portion, the fluid is heated by the heating unit 22. Although not shown in the figure, a high temp connecting hole is formed through the high temp water distributer 213, so that the fluid in the high temp mixing portion moves into the high temp maintaining portion according as the fluid in the high temp water tank 21 is discharged.

Here, the high temp maintaining portion is only heated using the high temp water distributer 213, and thus a temperature of the fluid in the high temp water tank 21 is less changed (especially, a heat loss of the high temp maintaining portion is prevented), the temperature of the fluid in the high temp water tank 21 is layered, and the fluid discharged from the high temp water outlet 212 is always maintained as the predetermined high temperature.

The low temp water tank 23 includes a low temp water inlet 231, a low temp water outlet 232 and a low temp water distributer 233. The fluid is flowed through the low temp water inlet 231. The fluid is discharged through the low temp water outlet 232. The low temp water distributer 231 divides an inside of the low temp water tank 23 into a low temp mixing portion and a high temp maintaining portion. The fluid flowed from the low temp water inlet 231 and the fluid in the low temp water tank 23 are mixed in the low temp mixing portion. The mixed fluid in the low temp mixing portion is maintained to be a predetermined low temperature in the low temp maintaining portion. In the low temp maintaining portion, the fluid is cooled by the cooling unit 22. Although not shown in the figure, a low temp connecting hole is formed through the low temp water distributer 233, so that the fluid in the low temp mixing portion moves into the low temp maintaining portion according as the fluid in the low temp water tank 23 is discharged.

Here, the low temp maintaining portion is only cooled using the low temp water distributer 233, and thus a temperature of the fluid in the low temp water tank 23 is less changed (especially, a heat loss of the low temp maintaining portion is prevented), the temperature of the fluid in the low temp water tank 23 is layered, and the fluid discharged from the low temp water outlet 232 is always maintained as the predetermined low temperature.

The fluid providing line 30 connects a first side of the artificial muscle module 10 with the artificial tank unit 20, to form a providing path for providing the fluid to the artificial muscle module 10. A providing temp sensor 35 may be positioned at the fluid providing line 30, to measure a temperature of the fluid provided to the artificial muscle module 10.

As illustrated in FIGS. 3 and 4, the fluid providing line 30 includes a first providing line 31 forming a path of the fluid discharged from the high temp water tank 21, a second providing line 32 forming a path of the fluid discharged from the low temp water tank 23, and a merging providing line 33 forming a path of the fluid providing to the artificial muscle module 10. The fluid having the predetermined high temperature and the fluid having the predetermined low temperature are mixed with each other in the merging providing line 33, and the mixed fluid is transmitted in the merging providing line 33. The providing temp sensor 35 may be positioned at the merging providing line 33.

Then, the first providing line 31 and the second providing line 32 are diverged from the merging providing line 33. Here, the first providing line 31 connects the high temp water outlet 212 with the temp control unit 60, the second providing line 32 connects the low temp water outlet 232 with the temp control unit 60, and the merging providing line 33 connects the fluid inlet 122 with the temp control unit 60.

The fluid collecting line 40 connects a second side of the artificial muscle module 10 with the fluid tank unit 20, to form a collecting path for collecting the fluid charged in the artificial muscle module 10. A collecting temp sensor 45 is positioned at the fluid collecting line 40, to measure a temperature of the fluid discharged from the artificial muscle module 10 (the fluid discharged through the fluid collecting line 40).

As illustrated in FIGS. 5 and 6, the fluid collecting line 40 includes a first collecting line 41 forming a path of the fluid collected to the high temp water tank 21, a second collecting line 42 forming a path of the fluid collected to the low temp water tank 23, and a distributing collecting line 43 forming a path of the fluid discharged from the artificial muscle module 10. The collecting temp sensor 45 may be positioned at the distributing collecting line 43.

Then, the first collecting line 41 and the second collecting line 42 are diverged from the distributing collecting line 43. Here, the first collecting line 41 connects the high temp water inlet 211 with the fluid distributing unit 70, the second collecting line 42 connects the low temp water inlet 232 with the fluid distributing unit 70, and the distributing collecting line 43 connects the fluid outlet 124 with the fluid distributing unit 70.

The circulation pump unit 50 is positioned at least one of the fluid providing line 30 and the fluid collecting line 40, to circulate the fluid between the artificial muscle module 10 and the fluid tank unit 20.

The circulation pump unit 50 is divided into a first pump 51 and a second pump 52. The first pump 51 is positioned at the fluid providing line 30, and the fluid in the fluid tank 20 is transmitted to the artificial muscle module 10 by the first pump 51. The second pump 52 is positioned at the fluid collecting line 40, and the fluid discharged from the artificial muscle module 10 is transmitted to the fluid tank unit 20 by the second pump 52.

In the present example embodiment, the first pump 51 is positioned at the merging providing line 33, but not limited thereto. The first pump 51 may be positioned at the first providing line 31 or the second providing line 32, and so on, so as to provide the fluid to the artificial muscle module 10 or to circulate the fluid between the fluid tank unit 20 and the artificial muscle module 10 stably.

In the present example embodiment, the second pump 52 is positioned at the distributing collecting line 43, but not limited thereto. The second pump 52 may be positioned at the first collecting line 41 or the second collecting line 42, and so on, so as to collect the fluid discharged from the artificial muscle module 10 to the fluid tank unit 20 or to circulate the fluid between the fluid tank unit 20 and the artificial muscle module 10 stably.

The temp control unit 60 is positioned at the fluid providing line 30. The temp control unit 60 controls temperature of the fluid to be provided to the artificial muscle module 11, using the fluid discharged from the high temp water tank 21 and the low temp water tank 23. Here, the fluid, the temperature of which is controlled by the temp control unit 60, may have a predetermined operating temperature, so that the shape of the heat reaction driving unit may be deformed.

For an example, the temp control unit 60, as illustrated in FIG. 3, may include a first control valve 61 controlling an amount of the fluid discharged from the high temp water tank 21, and a second control valve 62 controlling an amount of the fluid discharged from the low temp water tank 23. Then, the fluid passing through the first control valve 61 and the fluid passing through the second control valve 62 are mixed, so that the fluid passing through the temp control unit 60 has a predetermined operating temperature.

Alternatively, for another example, the temp control unit 60, as illustrated in FIG. 4, may further include a discharge control valve 63 discharging the fluid by controlling the amount of the fluid discharged from the low temp water tank 23 corresponding to the amount of the fluid discharged from the high temp water tank 21. Then, a ratio between the amount of the fluid discharged from the high temp water tank 21 and the amount of the fluid discharged from the low temp water tank 23 is controlled by the discharge control valve 62, and thus the fluid passing through the temp control unit 60 may have a predetermined operating temperature.

The fluid distributing unit 70 is positioned at the fluid collecting line 40. The fluid distributing unit 70 distributes the fluid of the fluid collecting line 40 into one of the high temp water tank 21 and the low temp water tank 23, according to a predetermined distributing condition.

Here, the predetermined distributing condition may be a temperature of the fluid collecting through the fluid collecting line 40. Then, when the temperature of the fluid collected through the fluid collecting line 40 is lower than a predetermined distributing temperature, the fluid distributing unit 70 distributes the fluid collecting through the fluid collecting line 40 to the low temp water tank 23. In addition, when the temperature of the fluid collected through the fluid collecting line 40 is higher than the predetermined distributing temperature, the fluid distributing unit 70 distributes the fluid collecting through the fluid collecting line 40 to the high temp water tank 21. In addition, when the temperature of the fluid collected through the fluid collecting line 40 is substantially same as the predetermined distributing temperature, the fluid distributing unit 70 distributes the fluid collecting through the fluid collecting line 40 to one of the high temp water tank 21 and the low temp water tank 23, based on an additional using condition.

Accordingly, since the fluid distributing unit 70 distributes the fluid collected through the fluid collecting line 40 to the high temp water tank 21 or the low temp water tank 23. The temperature of the fluid inside of the high temp water tank 21 is less changed, and the temperature of the fluid inside of the low temp water tank 23 is also less changed. In addition, power consumption for heating or cooling the fluid may be decreased, and the temperature of the fluid may be easily maintained in the fluid tank unit 20.

For an example, the fluid distributing unit 70 may include a first distributing valve 71 and a second distributing valve 72. The first distributing valve 71 distributes the fluid collected through the fluid collecting line 40 to the high temp water tank 21, and the second distributing valve 72 distributes the fluid collected through the fluid collecting line 40 to the low temp water tank 23. Then, the first distributing valve 71 or the second distributing valve 72 is operated according to the temperature of the fluid measured in the collecting temp sensor 45, so that the fluid collected through the fluid collecting line 40 is distributed to the high temp water tank 21 or the low temp water tank 23.

For another example, the fluid distributing unit 70 may further include a collected fluid distributing valve 73 distributing the fluid collected through the fluid collecting line 40 to the high temp water tank 21 or the low temp water tank 23. Then, the collected fluid distributing valve 73 is operated according to the temperature of the fluid measured in the collecting temp sensor 45, so as to distribute the fluid collected through the fluid collecting line 40 to the high temp water tank 21 or the low temp water tank 23.

The control unit 80 determines the predetermined operating temperature based on the displacement command for deforming the shape of the artificial muscle module 10, and then controls the circulation pump unit 50, the temp control unit 60 and the fluid distributing unit 70.

As illustrated in FIG. 2, the control unit 80 includes a displacement receiver 81, a temp determiner 82, a control unit controller 83, a distributing unit controller 84 and a pump controller 85.

The displacement receiver 81 receives a displacement command for deforming the shape of the artificial muscle module 10. The displacement command may be expressed variously, and includes information for an amount of displacement for contracting or relaxing the artificial muscle module 10.

The temp determiner 82 determines the operating temperature based on the displacement command. The operating temperature may be a predetermined value corresponding to the displacement command.

The control unit controller 83 controls an operation of the temp control unit 60. The control unit controller 83 controls the operation of the temp control unit 60 based on the operating temperature, so that the fluid having the predetermined operating temperature is formed for deforming the shape of the artificial muscle module 10 using the fluid discharged from the high temp water tank 21 and the low temp water tank 23. The control unit controller 83 receives the temperature measured by the providing temp sensor 35, to monitor the state of the operating temperature or to compensate the operating temperature of the fluid.

The distributing unit controller 84 controls an operation of the fluid distributing unit 70. The distributing unit controller 84 controls the operation of the fluid distributing unit 70 based on a predetermined distributing condition. The distributing unit controller 84 controls the operation of the fluid distributing unit 70, based on a comparison result between the temperature of the fluid collected through the fluid collecting line 40 and the predetermined distributing temperature, so that the fluid collected through the fluid collecting line 40 may be distributed to the high temp water tank 21 or the low temp water tank 23.

The pump controller 85 controls the circulation pump unit 50. The pump controller 85 controls the operation of the circulation pump unit 50, based on the displacement command or the operating temperature. The pump controller 85 controls the operation of the circulation pump unit 50, to circulate the fluid between the artificial muscle module 10 and the fluid tank unit 20.

The control unit 80 may further include at least one of a high temp water controller 86 and a low temp water controller 87.

The high temp water controller 86 controls the heating unit 22. The high temp water controller 86 operates the heating unit 22 according to the temperature of the fluid in the high temp water tank 21 (the fluid in the high temp maintaining portion), to maintain the temperature of the fluid in the high temp water tank 21 to be a relatively high temperature.

The low temp water controller 87 controls the cooling unit 24. The low temp water controller 87 operates the cooling unit 24 according to the temperature of the fluid in the low temp water tank 23 (the fluid in the low temp maintaining portion), to maintain the temperature of the fluid in the low temp water tank 23 to be a relatively low temperature lower than the relatively high temperature.

Hereinafter, the temp control unit 60 is explained in detail.

As illustrated in FIG. 3, in the temp control unit 60 in an example, the first control valve 61 is positioned at the first providing line 31, and the second control valve 62 is positioned at the second providing line 32.

When the circulation pump unit 50 is operated, the fluid having the predetermined high temperature is discharged through the high temp water outlet 212, and the fluid having the predetermined low temperature is discharged through the low temp water outlet 232. Here, as the operation of the control unit controller 83, an opening of the first control valve 61 and an opening of the second control valve 62 are controlled, so that the amount of the fluid passing through the first providing line 31 with the predetermined high temperature, and that passing through the second providing line 32 with the predetermined low temperature may be controlled.

The fluid passing through the first providing line 31 and the fluid passing through the second providing line 32 are summed or mixed, to form the fluid which has the predetermined operating temperature and is provided to the artificial muscle module 10. The fluid is transmitted through the merging providing line 33 due to the pumping of the circulation pump unit 50, to be transmitted to the artificial muscle module 10.

Here, the temp control unit 60 may further include a providing fluid mixer 64 mixing the fluid having the predetermined high temperature and the fluid having the predetermined low temperature, and thus the high temperature fluid and the low temperature fluid are stably mixed. Thus, the mixed fluid is to have the predetermined operating temperature, rapidly, and the heat may be prevented from being lost when the mixed fluid is transmitted through the merging providing line 33.

As illustrated in FIG. 4, in the temp control unit 60 in another example, the discharge control valve 63 includes a first inlet 632, a second inlet 633 and an operating fluid provider 635. The fluid discharged from the high temp water tank 21 is flowed through the first inlet 632, and the fluid discharged from the low temp water tank 23 is flowed through the second inlet 633. The fluid is discharged through the operating fluid provider 635. In addition, the discharge control valve 63 includes a discharge control path 631, an outlet diverging path 635, a discharge control block 636 and a control driver 637.

The discharge control path 631 connects the first inlet 632 with the second inlet 633, and forms a path of the fluid between the first inlet 632 and the second inlet 633.

The outlet diverging path 634 is diverged from the discharge control path 631, to be connected to the operating fluid provider 635, and the outlet diverging path 634 forms the path of the fluid between the discharge control path 631 and the operating fluid provider 635.

The discharge control block 636 is positioned at the discharge control path 631, with facing the outlet diverging path 634, and guides the fluid of the discharge control path 631 to the outlet diverging path 634. The discharge control block 636 is rotated or slidably moved in the discharge control path 631.

The control driver 637 drives the discharge control block 636.

Here, the first providing line 31 connects the high temp water outlet 212 of the high temp water tank 21 with the first inlet 632. The second providing line 32 connects the low temp water outlet 232 of the low temp water tank 23 with the second inlet 633. The merging providing line 33 connects the operating fluid provider 635 with the fluid inlet 122 of the artificial muscle module 10.

When the circulation pump unit 50 is operated, the fluid having the predetermined high temperature and the fluid having the predetermined low temperature are provided to the discharge control path 631. Here, as the operation of the control unit controller 83, the operation of the control driver 637 is controlled such that the discharge control block 636 moves, and thus a ratio of the amount of the fluid having the predetermined high temperature and the amount of the fluid having the predetermined low temperature may be controlled to be a predetermined ratio. Here, the predetermined ratio means that the amount of the fluid having the predetermined low temperature is (100−N), when the amount of the fluid having the predetermined high temperature is (N) and the amount of total fluid passing through the outlet diverging path 634 is (100).

The discharge control block 636 is operated to meet the predetermined ratio, and then the fluid having the predetermined operating temperature may be formed to be provided to the artificial muscle module 10. Thus, the fluid is transmitted through the merging providing line 33 due to the pumping of the first pump 51, to be transmitted to the artificial muscle module 10.

Here, the temp control unit 60 may further include a providing fluid mixer 64 mixing the fluid having the predetermined high temperature with the fluid having the predetermined low temperature, and thus the high temperature fluid and the low temperature fluid are stably mixed. Thus, the mixed fluid is to have the predetermined operating temperature, rapidly, and the heat may be prevented from being lost when the mixed fluid is transmitted through the merging providing line 33.

Hereinafter, the fluid distributing unit 70 is explained in detail.

As illustrated in FIG. 5, in the fluid distributing unit 70 in an example, the first distributing valve 71 is positioned at the first collecting line 41, and the second distributing valve 72 is positioned at the second collecting line 42.

When the circulation pump unit 50 is operated, the fluid discharged from the artificial muscle module 10 is transmitted in the distributing collecting line 43. As the operation of the distributing unit controller 84, an operation of the first distributing valve 71 or the second distributing valve 72 is controlled based on a predetermined distributing condition, so as to distribute the fluid collected through the fluid collecting line 40 to the high temp water tank 21 or the low temp water tank 23.

As illustrated in FIG. 6, in the fluid distributing unit 70 in another example, the collected fluid distributing valve 73 includes a first outlet 732, a second outlet 733 and a collecting fluid inlet 735. The fluid flowing in the high temp water tank 21 is discharged through the first outlet 732, and the fluid flowing in the low temp water tank 23 is discharged through the second outlet 733. The fluid discharged from the artificial muscle module 10 is flowed through the collecting fluid inlet 735. The collected fluid distributing valve 73 includes a collecting distributing path 731, an inlet diverging path 734, a collecting distributing block 736 and a distributing driver 737.

The collecting distributing path 731 connects the first outlet 732 with the second outlet 733, and forms a path of the fluid between the first outlet 732 and the second outlet 733.

The inlet diverging path 734 is diverged from the collecting distributing path 731, is connected to the collecting fluid inlet 735, and forms a path of the fluid between the collecting distributing path 731 and the collecting fluid inlet 735.

The collecting distributing block 736 is positioned at the collecting distributing path 731, with facing the inlet diverging path 734, and guides the fluid of the collecting distributing path 731 to the inlet diverging path 7341. The collecting distributing block 736 is rotated, or slidably moved in the collecting distributing path 731.

The distributing driver 737 operates the collecting distributing block 736.

Here, the first collecting line 41 connects the high temp water inlet 211 of the high temp water tank 21 with the first outlet 732. The second collecting line 42 connects the low temp water inlet 231 of the low temp water tank 23 with the second outlet 733. The distributing collecting line 43 connects the collecting fluid inlet 735 with the fluid outlet 124 of the artificial muscle module 10.

When the circulation pump unit 50 is operated, the fluid in the artificial muscle unit 10 is transmitted through the distributing collecting line 43, to be transmitted to the inlet diverging path 734. Here, as the operation of the distributing unit controller 84, the operation of the distributing driver 737 is controlled to move the collecting distributing block 736, so that the collecting distributing block 736 connects the first outlet 732 or the second outlet 733 with the collecting fluid inlet 735, and the fluid collected through the fluid collecting line 40 is distributed to the high temp water tank 21 or the low temp water tank 23. In addition, the collecting distributing block 736 closes the collecting fluid inlet 735 and prevents all fluid of the inlet distributing path 734 from being transmitted to the first outlet 732 and the second outlet 733.

The contraction of the artificial muscle module using the driving device according to the present example embodiment will be explained below referring to FIGS. 2 and 7.

When the displacement command for contracting the artificial muscle module 10 is received in the displacement receiver 81, the temp determiner 82 determines the operating temperature for contracting the artificial muscle module 10 based on the displacement command.

The pump controller 85 controls the operation of the circulation pump unit 50, to circulate the fluid between the fluid tank unit 20 with the artificial muscle module. Here, control unit controller 83 controls the operation of the temp control unit 60, to form the fluid having the predetermined operating temperature for contracting the artificial muscle module 10 in the merging providing line 33.

In addition, the fluid in the merging providing line 33 is provided to the artificial muscle module 10 to contract the heat reaction driving unit. Here, the fluid provided to the artificial muscle module 10 has the predetermined operating temperature for the contracting, and thus the heat reaction driving unit may be contracted accurately and precisely corresponding to the displacement command.

Further, the fluid discharged from the artificial muscle module 10 is transmitted to the fluid distributing unit 70 through the distributing collecting line 43, and the distributing unit controller 84 controls the operation of the fluid distributing unit 70 based on the predetermined distribution condition. Thus, the fluid collected through the fluid collecting line 40 is distributed to the high temp water tank 21 or the low temp water tank 23.

The relaxing of the artificial muscle module using the driving device according to the present example embodiment will be explained below referring to FIGS. 2 and 8.

First, when the displacement command for relaxing the artificial muscle module 10 is received in the displacement receiver 81, the temp determiner 82 determines the operating temperature for relaxing the artificial muscle module 10 based on the displacement command.

The pump controller 85 controls the operation of the circulation pump unit 50, to circulate the fluid between the fluid tank unit 20 with the artificial muscle module. Here, control unit controller 83 controls the operation of the temp control unit 60, to form the fluid having the predetermined operating temperature for relaxing the artificial muscle module 10 in the merging providing line 33.

In addition, the fluid in the merging providing line 33 is provided to the artificial muscle module 10 to relax the heat reaction driving unit. Here, the fluid provided to the artificial muscle module 10 has the predetermined operating temperature for the relaxing, and thus the heat reaction driving unit may be relaxed accurately and precisely corresponding to the displacement command.

Further, the fluid discharged from the artificial muscle module 10 is transmitted to the fluid distributing unit 70 through the distributing collecting line 43, and the distributing unit controller 84 controls the operation of the fluid distributing unit 70 based on the predetermined distribution condition. Thus, the fluid collected through the fluid collecting line 40 is distributed to the high temp water tank 21 or the low temp water tank 23.

In the driving device of the artificial muscle module, when the temperature of the fluid provided to the artificial muscle module 10 is higher than a reference temperature, the artificial muscle module 10 is contracted. When temperature of the fluid provided to the artificial muscle module 10 is lower than a reference temperature, the artificial muscle module 10 is relaxed. However, based on the kinds of the heat reaction driving unit, when the temperature of the fluid provided to the artificial muscle module 10 is higher than a reference temperature, the artificial muscle module 10 may be relaxed. Likewise, when temperature of the fluid provided to the artificial muscle module 10 is higher than a reference temperature, the artificial muscle module 10 is contracted.

Hereinafter, the driving method of the artificial muscle module using the driving device of the artificial muscle module. FIG. 9 is a driving method of the artificial muscle module using the driving device of the artificial muscle module of FIG. 1.

Referring to FIGS. 1 to 9, the method for driving the artificial muscle module includes contracting or relaxing the artificial muscle module 10.

The driving method of the artificial muscle module 10 includes a displacement receiving step S1, a temp determining step S2, a fluid circulating step S3, a temp control step S4, a module operating step S5 and a fluid distributing step S6, and may further include a fluid temp maintaining step S7.

In the displacement receiving step S1, the displacement command for deforming the shape of the artificial muscle module 10 is received. The displacement receiving step S1 may be performed according to the operation of the displacement receiver 81.

In a temp determining step S2, the operating temperature of the fluid for deforming the shape of the artificial muscle module 10 is determined based on the displacement command. The temp determining step S2 may be performed according to the operation of the temp determiner 82.

In the fluid circulating step S3, the fluid is circulated between the artificial muscle module 10 and the fluid tank unit 20. The fluid circulating step S3 may be performed according to the operation of the pump controller 85 and the circulation pump unit 50.

In the temp control step S4, temperature of the fluid is controlled by the temp control unit 60. Here, the fluid is controlled to be at the operating temperature using the fluid discharged from the high temp water tank 21 and the low temp water tank 23. In addition, the fluid having the operating temperature may deform the shape of the artificial muscle module 10. The temp control step S4 may be performed according to the operation of the control unit controller 83 and the temp control unit 60.

In the module operating step S5, the fluid at the operating temperature is provided to the artificial muscle module 10, and thus the shape of the artificial muscle module 10 is deformed due to the fluid having the predetermined operating temperature. The module operating step S5 may be performed due to an interaction between the fluid having the predetermined operating temperature and the artificial muscle module 10.

In the fluid distributing step S6, the fluid collected from the fluid collecting line 40 is distributed to the high temp water tank 21 or the low temp water tank 23, based on the distributing condition. The fluid distributing step S6 may be performed according to the operation of the distributing controller and the fluid distributing unit 70.

In the fluid temp maintaining step S7, the temperature of the fluid contained by the high temp water tank 21 is maintained to be the predetermined high temperature, or the temperature of the fluid contained by the low temp water tank 23 is maintained to be the predetermined low temperature, corresponding to the fluid flowed into or discharged from the fluid tank unit 20.

The fluid temp maintaining step S7 may be performed according to the operation of the high temp water controller 86 and the heating unit 22, or according to the operation of the low temp water controller 87 and the cooling unit 24.

The predetermined distributing condition may be a displacement command for deforming the shape of the artificial muscle module 10. Then, when the displacement command is for contracting the artificial muscle module 10, the temperature of the fluid in the artificial muscle module 10 is lower than that of the fluid provided to the artificial muscle module 10, and thus the fluid distributing unit 70 may distribute the fluid received through the fluid collecting line 40 to the low temp water tank 23. In addition, the temperature of the fluid received in the artificial muscle module 10 is higher than that of the fluid provided to the artificial muscle module 10, and thus the fluid distributing unit 70 may distribute the fluid collected through the fluid collecting line 40 to the high temp water tank 21.

Here, the distributing unit controller 84 controls the operation of the fluid distributing unit 70 based on the displacement command, so that the fluid collected through the fluid collecting line 40 may be distributed to the high temp water tank 21 or the low temp water tank 23.

The predetermined distributing condition mentioned above may be a water level of the high temp water tank 21 or a water level of the low temp water tank 23.

Then, when the water level of the high temp water tank 21 or that of the low temp water tank 23 becomes lower than a reference level, the fluid distributing unit 70 may distribute the fluid collected through the fluid collecting line 40 to the tank having the water level lower than the reference lever. In addition, comparing the water level of the high temp water tank 21 to that of the low temp water tank 23, the fluid distributing unit 70 may distribute the fluid collected through the fluid collecting line 40 to the tank having the relatively lower water level.

According to the present example embodiments, a flexible movement of the artificial muscle module 10 may be performed and a response of the artificial muscle module 10 may be increased according to a temperature of a fluid charged in the artificial muscle module, and energy efficiency may be increased. In addition, a predetermined high temperature fluid and a predetermined low temperature fluid are decided variously, and thus the operating temperature necessary for contracting or relaxing the heat reaction driving unit, and a displacement of the artificial muscle module 10 may be easily controlled. In addition, the predetermined high temperature and the predetermined low temperature may be easily maintained, and the temperature of the fluid in the fluid tank unit 20 is less changed, to meet the operating temperature in mixing the fluid, very conveniently.

In addition, the operating temperature may be easily performed, and an amount of the fluid provided to the artificial muscle module 10 may be easily controlled. In addition, the ratio of the fluid for performing the operating temperature may be easily controlled, and the fluid discharged from the fluid tank unit 20 may be easily stabilized. In addition, the fluid discharged from the artificial muscle module 10 may be easily collected, and the temperature of the fluid in the fluid tank unit 20 may be less changed. Thus, the temperature of the fluid in the fluid tank unit 20 may be easily maintained. In addition, the fluid discharged from the artificial muscle module 10 may be distributed more clearly, and thus the fluid tank unit 20 may be prevented from being malfunctioned in maintaining the temperature of the fluid according to the fluid collected from the fluid tank unit 20. In addition, the temperature of the fluid provided to the artificial muscle module 10 is variously changed to perform the flexibility of the artificial muscle module 10 very similar to a living body muscle.

Although the exemplary embodiments of the present invention have been described, it is understood that the present invention should not be limited to these exemplary embodiments but various changes and modifications can be made by one ordinary skilled in the art within the spirit and scope of the present invention as hereinafter claimed.

What is claimed is:
1. A driving device of an artificial muscle module, the artificial muscle module containing a fluid and a heat reaction driving unit deformed in a shape in response to temperature of the fluid, the driving device comprising:
a fluid tank unit comprising a high temperature water tank containing a relatively high temperature fluid, and a low temperature water tank containing a relatively low temperature fluid as compared to the relatively high temperature fluid, a fluid providing line connecting a first side of the artificial muscle module to the fluid tank unit, to provide the fluid to the artificial muscle module;

a fluid collecting line connecting a second side of the artificial muscle module to the fluid tank unit, to collect the fluid charged in the artificial muscle module;

a circulation pump unit positioned at at least one of the fluid providing line and the fluid collecting line, to circulate the fluid between the artificial muscle module and the fluid tank unit;

a temperature control unit for controlling temperature of the fluid to be provided to the artificial muscle module using the fluid discharged from the high temperature water tank and the low temperature water tank, wherein the temperature control unit is positioned at the fluid providing line; and a fluid distributing unit positioned at the fluid collecting line, and distributing the fluid in the fluid collecting line to the high temperature water tank or the low temperature water tank, wherein the temperature control unit comprises:

a discharge control valve for discharging the fluid by controlling the fluid discharged from the low temperature water tank considering an amount of the fluid discharged from the high temperature water tank, wherein a ratio between the amount of the fluid discharged from the high temperature water tank and an amount of the fluid discharged from the low temperature water tank is controlled by the discharge control valve, such that the fluid passing through the temperature control unit has a predetermined operating temperature.

2. The driving device of claim 1, wherein the fluid tank unit further comprises:

a heating unit for heating the fluid in the high temperature water tank, to maintain the fluid in the high temperature water tank to be in a predetermined high temperature.

3. The driving device of claim 1, wherein the fluid tank unit further comprises:

a cooling unit for cooling the fluid in the low temperature water tank, to maintain the fluid in the low temperature water to be in a predetermined low temperature.

4. A driving device of an artificial muscle module, the artificial muscle module containing a fluid and a heat reaction driving unit deformed in a shape in response to temperature of the fluid, the driving device comprising:

a fluid tank unit comprising a high temperature water tank containing a relatively high temperature fluid, and a low temperature water tank containing a relatively low temperature fluid as compared to the relatively high temperature fluid, a fluid providing line connecting a first side of the artificial muscle module to the fluid tank unit, to provide the fluid to the artificial muscle module;

a fluid collecting line connecting a second side of the artificial muscle module to the fluid tank unit, to collect the fluid charged in the artificial muscle module;

a circulation pump unit positioned at, at least one of the fluid providing line and the fluid collecting line, to circulate the fluid between the artificial muscle module and the fluid tank unit;

a temperature control unit for controlling temperature of the fluid to be provided to the artificial muscle module using the fluid discharged from the high temperature water tank and the low temperature water tank, wherein the temperature control unit is positioned at the fluid providing line; and a fluid distributing unit positioned at the fluid collecting line, and distributing the fluid in the fluid collecting line to the high temperature water tank or the low temperature water tank, wherein the temperature control unit comprises:

a first control valve for controlling an amount of the fluid discharged from the high temperature water tank; and a second control valve for controlling an amount of the fluid discharged from the low temperature water tank, wherein the amount of the fluid discharged from the high temperature water tank and that from the low temperature water tank are decided such that the fluid passing through the temperature control unit has a predetermined operating temperature.

5. A driving device of an artificial muscle module, the artificial muscle module containing a fluid and a heat reaction driving unit deformed in a shape in response to temperature of the fluid, the driving device comprising:

a fluid tank unit comprising a high temperature water tank containing a relatively high temperature fluid, and a low temperature water tank containing a relatively low temperature fluid as compared to the relatively high temperature fluid, a fluid providing line connecting a first side of the artificial muscle module to the fluid tank unit, to provide the fluid to the artificial muscle module;

a fluid collecting line connecting a second side of the artificial muscle module to the fluid tank unit, to collect the fluid charged in the artificial muscle module;

a circulation pump unit positioned at, at least one of the fluid providing line and the fluid collecting line, to circulate the fluid between the artificial muscle module and the fluid tank unit; a temperature control unit for controlling temperature of the fluid to be provided to the artificial muscle module using the fluid discharged from the high temperature water tank and the low temperature water tank, wherein the temperature control unit is positioned at the fluid providing line; and a fluid distributing unit positioned at the fluid collecting line, and distributing the fluid in the fluid collecting line to the high temperature water tank or the low temperature water tank, the fluid distributing unit comprises:

a first distributing valve for distributing the fluid collected from the fluid circulation line to the high temperature water tank; and a second distributing valve for distributing the fluid collected from the fluid circulation line to the low temperature water tank, wherein the first distributing valve or the second distributing valve is operated based on a predetermined distributing condition, so as to distribute the fluid collected from the fluid collecting line to the high temperature water tank or the low temperature water tank.

6. A driving device of an artificial muscle module, the artificial muscle module containing a fluid and a heat reaction driving unit deformed in a shape in response to temperature of the fluid, the driving device comprising:

a fluid tank unit comprising a high temperature water tank containing a relatively high temperature fluid, and a low temperature water tank containing a relatively low temperature fluid as compared to the relatively high temperature fluid, a fluid providing line connecting a first side of the artificial muscle module to the fluid tank unit, to provide the fluid to the artificial muscle module;

a fluid collecting line connecting a second side of the artificial muscle module to the fluid tank unit, to collect the fluid charged in the artificial muscle module;

a circulation pump unit positioned at, at least one of the fluid providing line and the fluid collecting line, to circulate the fluid between the artificial muscle module and the fluid tank unit;

a temperature control unit for controlling temperature of the fluid to be provided to the artificial muscle module using the fluid discharged from the high temperature water tank and the low temperature water tank, wherein the temperature control unit is positioned at the fluid providing line; and a fluid distributing unit positioned at the fluid collecting line, and distributing the fluid in the fluid collecting line to the high temperature water tank or the low temperature water tank, wherein the fluid distributing unit comprises:

a collected fluid distributing valve for distributing the fluid collected from the fluid collecting line to the high temperature water tank or the low temperature water tank, wherein the collected fluid distributing valve is operated based on a predetermined distributing condition, so as to distribute the fluid collected from the fluid collecting line to the high temperature water tank or the low temperature water tank.

7. The driving device of claim 1, further comprising:

a control unit for determining an operating temperature of a fluid for deforming a shape of the artificial muscle module based on a displacement command, to control the circulation pump unit, the temperature control unit and the fluid distributing unit.

8. A driving method of an artificial muscle module, the driving method comprising steps for:

receiving a displacement command for deforming a shape of the artificial muscle module;

determining an operating temperature of a fluid for deforming the shape of the artificial muscle module based on the displacement command;

circulating by a circulation pump unit, the fluid between the artificial muscle module and the fluid tank unit;

controlling, by a temperature control unit, a fluid to be at the operating temperature using a fluid discharged from a high temperature water tank and a low temperature water tank in a fluid tank;

providing, by a fluid providing line, the fluid at the operating temperature to the artificial muscle module; and collecting, by a fluid collecting line, the fluid from the artificial muscle module and distributing the fluid to the high temperature water tank or the low temperature water tank, based on a distributing condition, wherein the circulation pump unit is positioned at, at least one of the fluid providing line and the fluid collecting line, the temperature control unit includes a discharge control valve, the controlling includes controlling the fluid discharged by the discharge control valve from the low temperature water tank considering an amount of the fluid discharged from the high temperature water tank, and a ratio between the amount of the fluid discharged from the high temperature water tank and an amount of the fluid discharged from the low temperature water tank is controlled by the discharge control valve, such that the fluid passing through the temperature control unit has a predetermined operating temperature.

9. The driving method of claim 8, further comprising:

maintaining the temperature of the fluid in the high temperature water tank to be a predetermined high temperature, or maintaining the temperature of the fluid in the low temperature water tank to be a predetermined low temperature, corresponding to the fluid flowed into or discharged from the fluid tank unit.

* * * * *